United States Patent [19]

Howard, Jr.

[11] Patent Number: 5,703,065
[45] Date of Patent: Dec. 30, 1997

US005703065A

[54] HETEROARYLAMINO AND HETEROARYLSULFONAMIDO SUBSTITUTED 3-BENYZLAMINOMETHYL PIPERIDINES AND RELATED COMPOUNDS

[75] Inventor: Harry R. Howard, Jr., Bristol, Conn.

[73] Assignee: Pfizer Inc., New York, N.Y.

[21] Appl. No.: 615,257

[22] PCT Filed: Jul. 18, 1994

[86] PCT No.: PCT/IB94/00221

§ 371 Date: May 7, 1996

§ 102(e) Date: May 7, 1996

[87] PCT Pub. No.: WO95/03908

PCT Pub. Date: Mar. 23, 1995

Related U.S. Application Data

[63] Continuation of Ser. No. 123,306, Sep. 17, 1993, abandoned.

[51] Int. Cl.$^6$ ............ C07D 211/56; C07D 277/42; C07D 417/12; A61K 31/425
[52] U.S. Cl. ............ 514/183; 514/210; 514/212; 514/256; 514/269; 514/318; 514/326; 514/383; 514/362; 514/363; 514/364; 514/369; 514/370; 514/372; 514/376; 514/377; 514/380; 514/384; 514/398; 514/422; 540/480; 540/481; 540/605; 544/298; 544/333; 546/194; 546/208; 546/209; 546/210; 546/213; 546/276.4; 548/127; 548/128; 548/129; 548/130; 548/135; 548/13; 548/138; 548/141; 548/132; 548/133; 548/143; 548/144; 548/145; 548/225; 548/226; 548/223; 548/243; 548/245; 548/255; 548/263.2; 548/264.8; 548/183; 548/189; 548/199; 548/206; 548/213; 548/214; 548/518
[58] Field of Search ............ 546/16, 209, 213, 546/208, 210; 514/278, 326

[56] References Cited

U.S. PATENT DOCUMENTS

| | | | |
|---|---|---|---|
| 5,234,946 | 8/1993 | Takezawa et al. | 514/444 |
| 5,340,826 | 8/1994 | Rosen et al. | 514/351 |
| 5,519,033 | 5/1996 | Rosen et al. | 514/305 |

FOREIGN PATENT DOCUMENTS

| | | |
|---|---|---|
| WO9109844 | 7/1991 | WIPO. |
| WO9300331 | 1/1993 | WIPO. |
| WO9301170 | 1/1993 | WIPO. |
| WO9413663 | 6/1994 | WIPO. |

OTHER PUBLICATIONS

P. W. Mantyh, Ann. N.Y. Acad. Sci., 632:263–271 (1991).
P. W. Mantyh et al., Proc. Natl. Acad. Sci., 86:5193–5197 (1989).
B. D. Gitter et al., J. Neuroimmunol., 51:101–108 (1994).
J. Luber–Narod, J. Immunol., 152:819–824 (1994).
W. S. T. Griffin et al., Proc. Natl. Acad. Sci., USA, 86:7611–7615 (1989).
J. A. Wood et al., Brain Res., 629:245–252 (1993).
B. T. Hyman et al., Ann. Neurol., 32(6):818–820 (1992).
S. C. Lee et al., J. Neuroimmunol., 46:19–24 (1993).
S. H. Taylor, J. Cardiovasc. Pharm., 20:S103–S108 (1992).
L. Pradier et al., J. Neurochem., 61(5):1850–1858 (1993).
F. C. Martin et al., Brain Res., 599:13–18 (1992).
C. M. Lee, J. Neurochem., 59(2):406–414 (1992).
J. C. Beaujouan et al., Peptides, 12:813–820 (1991).
C. L. Johnson et al., J. Neurochem., 58(2):471–477 (1992).

*Primary Examiner*—Mukund J. Shah
*Assistant Examiner*—Deepak R. Rao
*Attorney, Agent, or Firm*—Peter C. Richardson; Paul H. Ginsburg; Bryan C. Zielinski

[57] ABSTRACT

The invention relates to compounds of the formula

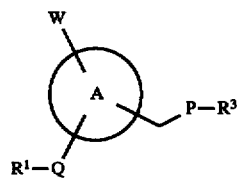

and to pharmaceutically acceptable salts thereof, wherein A, W, P, $R^3$, Q and $R^1$ are as defined herein. The compounds of formula I, and pharmaceutically acceptable salts thereof, are substance P antagonists and as such are useful in the treatment of various inflammatory and central nervous system disorders.

13 Claims, No Drawings

HETEROARYLAMINO AND HETEROARYLSULFONAMIDO SUBSTITUTED 3-BENYZLAMINOMETHYL PIPERIDINES AND RELATED COMPOUNDS

This is a national stage application, filed pursuant to 35 U.S.C. §9371, of PCT international application number PCT/IB94/00221, filed Jul. 18, 1994, published as WO95/07908 Mar. 23, 1995. This application is a continuation of U.S. application Ser. No. 08/123,306, filed Sep. 17, 1993, now abandoned.

BACKGROUND OF THE INVENTION

The present invention relates to novel heteroarylamino and heteroarylsulfonamido substituted 3-benzylaminomethylpiperidines substituted benzylamino nitrogen containing non-aromatic heterocycles, pharmaceutical compositions comprising such compounds and the use of such compounds in the treatment and prevention of inflammatory and central nervous system disorders, as well as several other disorders. The pharmaceutically active compounds of this invention are substance P receptor antagonists. This invention also relates to novel intermediates used in the synthesis of such substance P receptor antagonists.

Substance P is a naturally occurring undecapeptide belonging to the tachykinin family of peptides, the latter being named because of their prompt stimulatory action on smooth muscle tissue. More specifically, substance P is a pharmacologically active neuropeptide that is produced in mammals and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has been shown to be involved in the transmission of pain or migraine (see B. E. B. Sandberg et al., *Journal of Medicinal Chemistry*, 25, 1009 (1982)), as well as in central nervous system disorders such as anxiety and schizophrenia, in respiratory and inflammatory diseases such as asthma and rheumatoid arthritis, respectively, in rheumatic diseases such as fibrositis, and in gastrointestinal disorders and diseases of the GI tract such as ulcerative colitis and Crohn's disease, etc. (see D. Regoli in "Trends in Cluster Headache," edited by F. Sicuteri et al., Elsevier Scientific Publishers, Amsterdam, pp. 85–95 (1987)).

Quinuclidine, piperidine, and azanorbornane derivatives and related compounds that exhibit activity as substance P receptor antagonists are referred to in U.S. patent application Ser. No. 566,338 filed Nov. 20, 1989, U.S. patent application Ser. No. 724,268, filed Jul. 1, 1991, PCT Patent Application PCT/US 91/02853, filed Apr. 25, 1991, PCT Patent Application PCT/US 91/03369, filed May 14, 1991, PCT Patent Application PCT/US 91/05776, filed Aug. 20, 1991, PCT Patent Application PCT/US 92/00113, filed Jan. 17, 1992, PCT Patent Application PCT/US 92/03571, filed May 5, 1992, PCT Patent Application PCT/US 92/03317, filed Apr. 28, 1992, PCT Patent Application PCT/US 92/04697, filed Jun. 11, 1992, U.S. patent application Ser. No. 766,488, filed Sep. 26, 1991, U.S. patent application Ser. No. 790,934, filed Nov. 12, 1991, PCT Patent Application PCT/US 92/04002, filed May 19, 1992, Japanese Patent Application No. 065337/92, filed Mar. 23, 1992, and U.S. patent application Ser. No. 932,392, filed Aug. 19, 1992.

SUMMARY OF THE INVENTION

The present invention relates to compounds of the formula

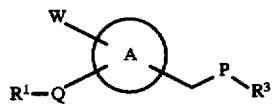

wherein ring A is an aryl group selected from phenyl, naphthyl, thienyl, dihydroquinolinyl and indolinyl, and wherein the $-CH_2PR^3$ sidechain is attached to a carbon atom of ring A;

P is $NR^2$, O, S, SO or $SO_2$;

Q is $SO_2$, NH,

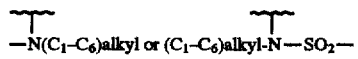

wherein the point of attachment of said

to ring A is the nitrogen atom and the point of attachment to $R^1$ is the sulfur atom;

W is hydrogen, $(C_1-C_6)$alkyl, $S-(C_1-C_3)$alkyl, halo or $(C_1-C_6)$alkoxy optionally substituted with from one to three fluorine atoms;

$R^1$ is a four to six membered heterocyclic ring containing from one to three heteroatoms selected from sulfur, nitrogen and oxygen (e.g., thiazolyl, pyrrolyl, thienyl, triazolyl, oxazolyl, oxadiazolyl, thiadiazolyl or imidazolyl), wherein said heterocyclic ring may optionally be substituted with from one to three substituents, preferably with from zero to two substituents, independently selected from phenyl, $(C_1-C_6)$alkyl optionally substituted with from one to three fluorine atoms, $(C_1-C_6)$alkoxy optionally substituted with from one to three fluorine atoms and halo;

$R^2$ is hydrogen or $-CO_2(C_1-C_{10})$alkyl;

$R^3$ is selected from

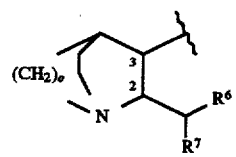

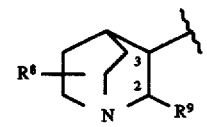

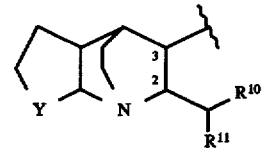

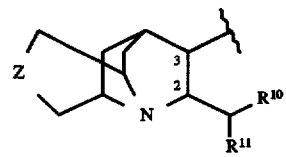

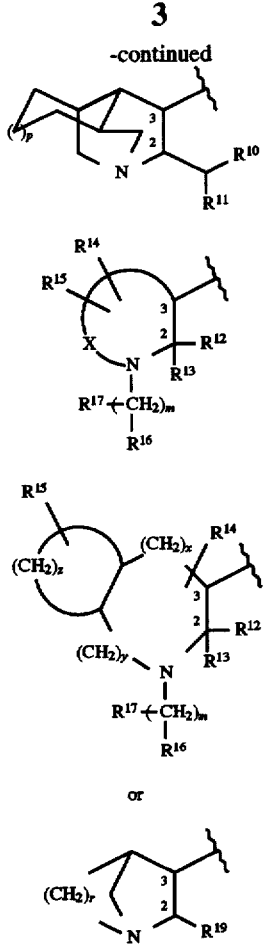

wherein $R^6$ and $R^{10}$ are independently selected from furyl, thienyl, pyridyl, indolyl, biphenyl and phenyl, wherein said phenyl may optionally be substituted with one or two substituents independently selected from halo, $(C_1-C_{10})$ alkyl optionally substituted with from one to three fluorine atoms, $(C_1-C_{10})$alkoxy optionally substituted with from one to three fluorine atoms, carboxy, benzyloxycarbonyl and $(C_1-C_3)$ alkoxy-carbonyl;

$R^7$ is selected from $(C_3-C_4)$ branched alkyl, $(C_5-C_6)$ branched alkenyl, $(C_5-C_7)$ cycloalkyl, and the radicals named in the definition of $R^6$;

$R^8$ is hydrogen or $(C_1-C_6)$ alkyl;

$R^9$ and $R^{19}$ are independently selected from phenyl, biphenyl, naphthyl, pyridyl, benzhydryl, thienyl or furyl, and $R^9$ and $R^{19}$ may optionally be substituted with from one to three substituents independently selected from halo, $(C_1-C_{10})$ alkyl optionally substituted with from one to three fluorine atoms and $(C_1-C_{10})$ alkoxy optionally substituted with from one to three fluorine atoms;

Y is $(CH_2)_l$ wherein l is an integer from one to three, or Y is a group of the formula

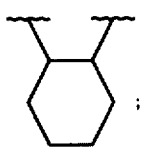

(J)

Z is oxygen, sulfur, amino, $(C_1-C_3)$alkylamino or $(CH_2)_n$ wherein n is zero, one or two;

x is zero, one or two;

y is zero, one or two;

z is three, four or five;

o is two or three, p is zero or one;

r is one, two or three;

the ring containing $(CH_2)_z$ may contain from zero to three double bonds, and one of the carbon atoms of $(CH_2)_z$ may optionally be replaced by oxygen, sulfur or nitrogen;

$R^{11}$ is thienyl, biphenyl or phenyl optionally substituted with one or two substituents independently selected from halo, $(C_1-C_{10})$ alkyl optionally substituted with from one to three fluorine atoms and $(C_1-C_{10})$ alkoxy optionally substituted with from one to three fluorine atoms;

X is $(CH_2)_q$ wherein q is an integer from 1 to 6, and wherein any one of the carbon-carbon single bonds in said $(CH_2)_q$ may optionally be replaced by a carbon-carbon double bond, and wherein any one of the carbon atoms of said $(CH_2)_q$ may optionally be substituted with $R^{14}$, and wherein any one of the carbon atoms of said $(CH_2)_q$ may optionally be substituted with $R^{15}$;

m is an integer from 0 to 8, and any one of the carbon-carbon single bonds of $(CH_2)_m$, wherein both carbon atoms of such bond are bonded to each other and to another carbon atom of the $(CH_2)_m$ chain, may optionally be replaced by a carbon-carbon double bond or a carbon-carbon triple bond, and any one of the carbon atoms of said $(CH_2)_m$ may optionally be substituted with $R^{17}$;

$R^{12}$ is a radical selected from hydrogen, $(C_1-C_6)$ straight or branched alkyl, $(C_3-C_7)$ cycloalkyl wherein one of the carbon atoms may optionally be replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl-$(C_2-C_6)$ alkyl, benzhydryl and benzyl, wherein the point of attachment on $R^{12}$ is a carbon atom unless $R^{12}$ is hydrogen, and wherein each of said aryl and heteroaryl groups and the phenyl moieties of said benzyl, phenyl-$(C_2-C_6)$ alkyl and benzhydryl may optionally be substituted with one or more substituents independently selected from halo, nitro, $(C_1-C_{10})$ alkyl optionally substituted with from one to three fluorine atoms, $(C_1-C_{10})$ alkoxy optionally substituted with from one to three fluorine atoms, amino, hydroxy-$(C_1-C_6)$alkyl, $(C_1-C_6)$alkoxy-$(C_1-C_6)$alkyl, $(C_1-C_6)$-alkylamino,

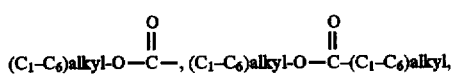

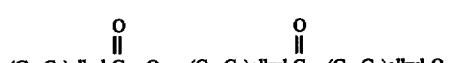

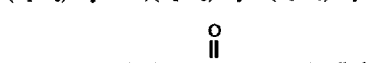

-continued

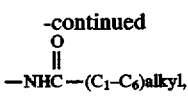

and wherein one of the phenyl moieties of said benzhydryl may optionally be replaced by naphthyl, thienyl, furyl or pyridyl;

$R^{13}$ is hydrogen, phenyl or $(C_1-C_6)$alkyl;

or $R^{12}$ and $R^{13}$, together with the carbon to which they are attached, form a saturated carbocyclic ring having from 3 to 7 carbon atoms wherein one of said carbon atoms that is neither the point of attachment of the spiro ring nor adjacent to such point of attachment may optionally be replaced by oxygen, nitrogen or sulfur;

$R^{14}$ and $R^{15}$ are each independently selected from hydrogen, hydroxy, halo, amino, oxo (=O), cyano, hydroxy-$(C_1-C_6)$alkyl, $(C_1-C_6)$alkoxy-$(C_1-C_6)$alkyl, $(C_1-C_6)$alkylamino, di-$(C_1-C_6)$alkylamino, $(C_1-C_6)$alkoxy,

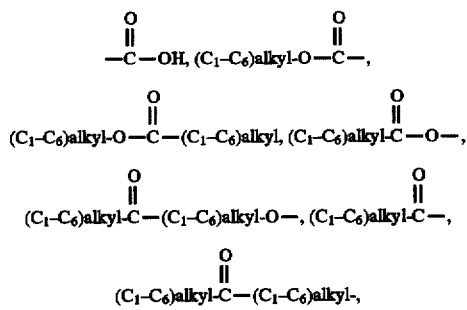

and the radicals set forth in the definition of $R^{12}$;

$R^{16}$ is

$NHCH_2R^{18}$, $SO_2R^{18}$, $CO_2H$ or one of the radicals set forth in any of the definitions of $R^{12}$, $R^{14}$ and $R^{15}$;

$R^{17}$ is oximino (=NOH) or one of the radicals set forth in any of the definitions of $R^{12}$, $R^{14}$ and $R^{15}$; and $R^{18}$ is $(C_1-C_6)$alkyl, hydrogen, phenyl or phenyl $(C_1-C_6)$alkyl;

with the proviso that (a) when m is 0, one of $R^{16}$ and $R^{17}$ is absent and the other is hydrogen, (b) when $R^3$ is a group of the formula VIII, $R^{14}$ and $R^{15}$ cannot be attached to the same carbon atom, (c) when $R^{14}$ and $R^{15}$ are attached to the same carbon atom, then either each of $R^{14}$ and $R^{15}$ is independently selected from hydrogen, fluoro, $(C_1-C_6)$alkyl, hydroxy-$(C_1-C_6)$alkyl and $(C_1-C_6)$alkoxy-$(C_1-C_6)$alkyl, or $R^{14}$ and $R^{15}$, together with the carbon to which they are attached, form a $(C_3-C_6)$ saturated carbocyclic ring that forms a spiro compound with the nitrogen-containing ring to which they are attached; (d) when $R^1$ is amino, $(C_1-C_6)$ alkylamino, di-$(C_1-C_6)$alkylamino or

$R^3$ is a group of the formula II, III, IV, V or VI, and (e) when $R^{14}$ or $R^{15}$ is attached to a carbon atom of X or $(CH_2)_y$ that is adjacent to the ring nitrogen, then $R^{14}$ or $R^{15}$, respectively, must be a substituent wherein the point of attachment is a carbon atom.

The present invention also relates to the pharmaceutically acceptable acid addition and base salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium calcium and magnesium, etc.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined as above.

The term "one or more substituents," as used herein, includes from one to the maximum number of substituents possible based on the number of available bonding sites.

Preferred compounds of the formula I include those wherein the substituents at positions "2" and "3" of the nitrogen containing ring of $R^3$ are in a cis configuration. When $R^3$ is a group of the formula VII or VIII, "a cis configuration," as used herein, means that the non-hydrogen substituent at position "3" is cis to $R^{12}$.

Other preferred compounds of the formula I are those wherein $R^3$ is a group of the formula II, III, VII or IX; $R^2$ is hydrogen; ring A is phenyl; W is $(C_1-C_3)$alkoxy optionally substituted with from one to five fluorine atoms; Q is

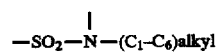

and $R^1$ is 5-thiazolyl.

More preferred compounds of the formula I are the foregoing preferred compounds wherein: (a) $R^3$ is a group of the formula III and $R^9$ is benzhydryl; (b) $R^3$ is a group of the formula VII, $R^{12}$ is phenyl, each of $R^{13}$, $R^{14}$, $R^{15}$ and $R^{16}$ is hydrogen, m is zero and X is —$(CH_2)_3$—; or (c) $R^3$ is a group of the formula IX, r is two and $R^{19}$ is benzhydryl.

Other more preferred compounds of the formula I are those wherein: (a) $R^3$ is a group of the formula III wherein the substituents at positions "2" and "3" of the nitrogen containing ring are in the cis configuration, $R^9$ is benzhydryl and ring A is phenyl; (b) $R^3$ is a group of the formula VII wherein $R^{12}$ and the substituent at position "3" of the nitrogen containing ring are in the cis configuration, ring A is phenyl, $R^{12}$ is phenyl, each of $R^2$, $R^{13}$, $R^{14}$, $R^{15}$ and $R^{16}$ is hydrogen, m is zero, W is methoxy, trifluoromethoxy or isopropoxy, X is —$(CH_2)_3$—, Q is

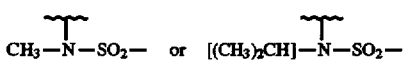

and R[1] is 2,4-dimethyl-5-thiazolyl; or (c) R[3] is a group of the formula IX wherein the substituents at positions "2" and "3" of the nitrogen containing ring are in the cis configuration, R[19] is benzhydryl, r is two and ring A is phenyl.

Especially preferred compounds of this invention are those wherein R[3] is a group of the formula VII, R[17] is phenyl, each of R[13], R[14], R[15] and R[16] is hydrogen, m is zero, X is —(CH$_2$)$_3$—, ring A is phenyl, W is selected from OCF$_3$, OCH$_3$, isopropoxy, OCHF$_2$ and OCH$_2$CF$_3$,

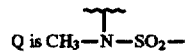

and R[1] is 2,4-dimethyl-5-thiazolyl.

Specific preferred compounds of the formula I include the following:

2,4-dimethylthiazole-5-sulfonic acid [4-methoxy-3-((2S,3S)-2-phenylpiperidin-3-ylaminomethyl)phenyl]-methylamide;

N-(4,5-dimethylthiazol-2-yl)-N-[4-methoxy-3-((2S,3S)-2-phenylpiperidin-3-yl-aminomethyl)phenyl]-methanesulfonamide;

{5-[(4,5-dimethylthiazol-2-yl)methylamino]-2-methoxybenzyl}-((2S,3S)-2-phenylpiperidin-3-yl)amine;

{5-(4,5-dimethylthiazol-2-ylamino)-2-methoxybenzyl}-((2S,3S)-2-phenylpiperidin-3-ylamine;

4,5-dimethylthiazole-2-sulfonic acid methyl-[3-((2S,3S)-2-phenylpiperidin-3-ylaminomethyl)-4-trifluoromethoxyphenyl]-amide;

2,4-dimethylthiazole-5-sulfonic acid [4-isopropoxy-3-((2S,3S)-2-phenylpiperidin-3-ylaminomethyl)phenyl]-methylamide;

2,4-dimethylthiazole-5-sulfonic acid [4-isopropoxy-3-((2S,3S)-2-phenylpiperidin-3-ylaminomethyl)phenyl]-isopropylamide;

2,4-dimethylthiazole-5-sulfonic acid [4-methoxy-3-((2S,3S)-2-phenylpiperidin-3-ylaminomethyl)phenyl]-isopropylamide;

2,4-dimethylthiazole-5-sulfonic acid [4-methoxy-3-((2S,3S)-2-phenylpiperidin-3-ylaminomethyl)phenyl]-isobutylamide; and 2,4-dimethylthiazole-5-sulfonic acid [4-isopropoxy-3-((2S,3S)-2-phenylpiperidin-3-ylaminomethyl)phenyl]-isobutylamide.

Examples of other compounds of the formula I are:

2-trifluoromethylthiazole-5-sulfonic acid {4-methoxy-3[((2S,3S)-2-phenylpiperidin-3-ylamino)methyl]phenyl}-methylamide;

2,4-bis-trifluoromethylthiazole-5-sulfonic acid {4-methoxy-3-[((2S,3S)-2-phenylpiperidin-3-ylamino)methyl]phenyl}-methylamide;

oxazole-5-sulfonic acid {4-methoxy-3-[((2S,3S)-2-phenylpiperidin-3-ylamino)methyl]phenyl}-methylamide;

2,5-dimethylthiazole-4-sulfonic acid {4-methoxy-3-[((2S,3S)-2-phenylpiperidin-3-ylamino)methyl]phenyl}-methylamide;

4,5-dimethylthiazole-2-sulfonic acid {4-methoxy-3-[((2S,3S)-2-phenylpiperidin-3-ylamino)methyl]phenyl}-methylamide;

thiazole-5-sulfonic acid {4-methoxy-3-[((2S,3S)-2-phenylpiperidin-3-ylamino)methyl]phenyl}-methylamide;

2,5-dimethylthiazole-4-sulfonic acid {4-trifluoromethoxy-3-[((2S,3S)-2-phenylpiperidin-3-ylamino)methyl]phenyl}-methylamide;

2,5-dimethylthiazole-4-sulfonic acid {4-isopropoxy-3-[((2S,3S)-2-phenylpiperidin-3-ylamino)methyl]phenyl}-methylamide;

2,5-dimethylthiazole-4-sulfonic acid {3-[(2-benzhydryl-1-azabicyclo[2.2.2]oct-3-ylamino)methyl]-4-methoxyphenyl}-methylamide;

2,5-dimethylthiazole-4-sulfonic acid {3-[(-2-benzhydryl-1-azabicyclo[2.2.1]hept-3-ylamino)methyl]-4-methoxyphenyl}-methylamide;

thiophene-2-sulfonic acid {4-methoxy-3-[((2S,3S)-2-phenylpiperidin-3-ylamino)methyl]phenyl}-methylamide;

[1,3,4]thiadiazole-2-sulfonic acid {4-methoxy-3-[((2S,3S)-2-phenylpiperidin-3-ylamino)methyl]phenyl}-methylamide;

thiophene-2-sulfonic acid {4-methoxy-3-[((2S,3S)-2-phenylpiperidin-3-ylamino)methyl]phenyl}-amide;

thiophene-2-sulfonic acid {4-isopropoxy-3-[((2S,3S)-2-phenylpiperidin-3-ylamino)methyl]phenyl}-methylamide;

[5-(2,4-dimethylthiazole-5-sulfonyl)-2-methoxybenzyl]-[(2S,3S)-2-phenylpiperidin-3-yl]-amine;

[5-(2,4-dimethylthiazole-5-sulfonyl)-2-isopropoxybenzyl]-[(2S,3S)-2-phenylpiperidin-3-yl]-amine;

[5-(2,4-dimethylthiazole-5-sulfonyl)-2-trifluoromethoxybenzyl]-[(2S,3S)-2-phenylpiperidin-3-yl]-amine;

[2-methoxy-5-([1,2,3]thiadiazole-5-sulfonyl)benzyl]-[(2S,3S)-2-phenylpiperidin-3-yl]-amine;

[2-methoxy-5-(pyridine-2-sulfonyl)benzyl]-[(2S,3S)-2-phenylpiperidin-3-yl]-amine;

[2-methoxy-5-(pyridine-3-sulfonyl)benzyl]-[(2S,3S)-2-phenylpiperidin-3-yl]-amine;

[2-methoxy-5-(pyrimidine-2-sulfonyl)benzyl]-[(2S,3S)-2-phenylpiperidin-3-yl]-amine; and

[2-methoxy-5-(thiophene-2-sulfonyl)benzyl]-[(2S,3S)-2-phenylpiperidin-3-yl]-amine.

The present invention also relates to compounds of the formulae

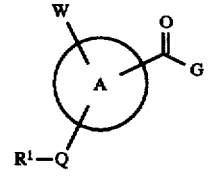

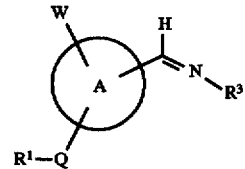

and

-continued

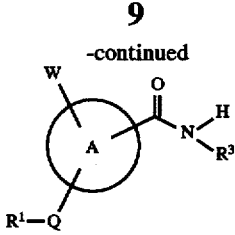

XII wherein ring A, Q, $R^1$, $R^3$ and W are defined as above and G is hydrogen. These compounds may be used as intermediates in the synthesis of compounds of the formula I.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, urinary incontinence, gastrointestinal disorders such as emesis and colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, urinary incontinence, gastrointestinal disorders such as emesis and colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

The present invention also relates to a pharmaceutical composition for antagonizing the effects of substance P in a mammal, including a human, comprising a substance P antagonizing amount of a compound of the formula I, or a pharmaceutically acceptable salt thereof, and a pharmaceutically acceptable carrier.

The present invention also relates to a method of antagonizing the effects of substance P in a mammal, including a human, comprising administering to said mammal a substance P antagonizing amount of a compound of the formula I, or a pharmaceutically acceptable salt thereof.

The present invention also relates to a pharmaceutical composition for treating or preventing a disorder in a mammal, including a human, resulting from an excess of substance P, comprising a substance P antagonizing amount of a compound of the formula I, or a pharmaceutically acceptable salt thereof, and a pharmaceutically acceptable carrier.

The present invention also relates to a method of treating or preventing a disorder in a mammal, including a human, resulting from an excess of substance P, comprising administering to said mammal a substance P antagonizing amount of a compound of the formula I, or a pharmaceutically acceptable salt thereof.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, urinary incontinence, gastrointestinal disorders such as emesis and colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, urinary incontinence, gastrointestinal disorders such as emesis and colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention which is effected or facilitated by a decrease in substance P mediated neurotransmission, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in treating or preventing such disorder, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in treating or preventing such disorder.

The compounds of the formula I have chiral centers and therefore exist in different enantiomeric forms. This invention relates to all optical isomers and all stereoisomers of compounds of the formula I, and mixtures thereof.

DETAILED DESCRIPTION OF THE INVENTION

The compounds of the formula I may be prepared as described in the following reaction schemes and discussion. Unless otherwise indicated, ring A, P, Q, W, $R^1$, $R^2$, $R^3$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, X, Z, Y, m, n, o, p, q, r, x, y, and z, and structural formulas I, II, III, IV, V, VI, VII, VIII, IX, X, XI and XII in the reaction schemes and discussion that follow are defined as above.

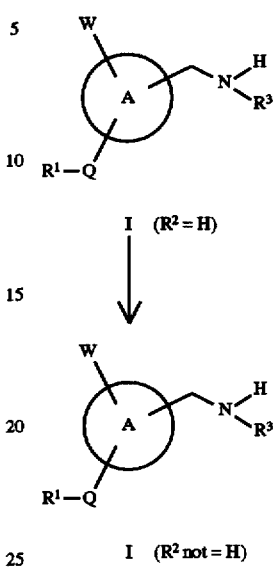

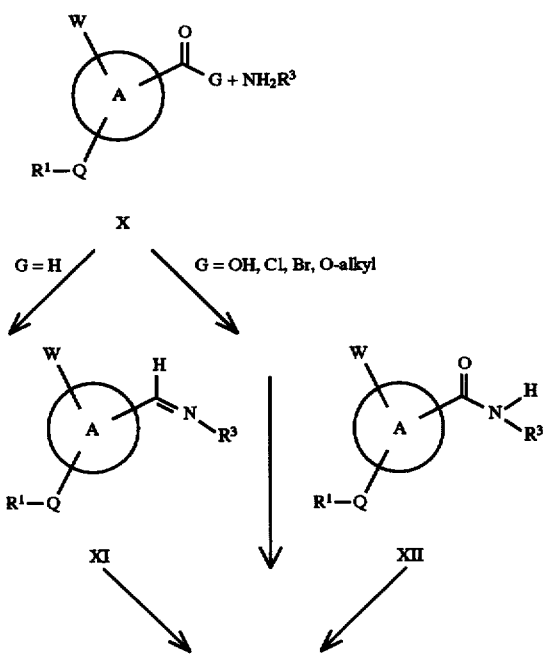

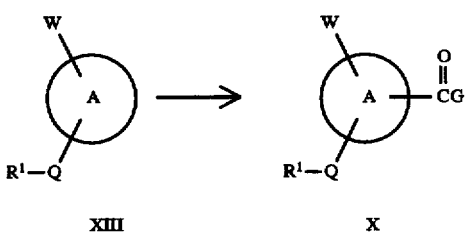

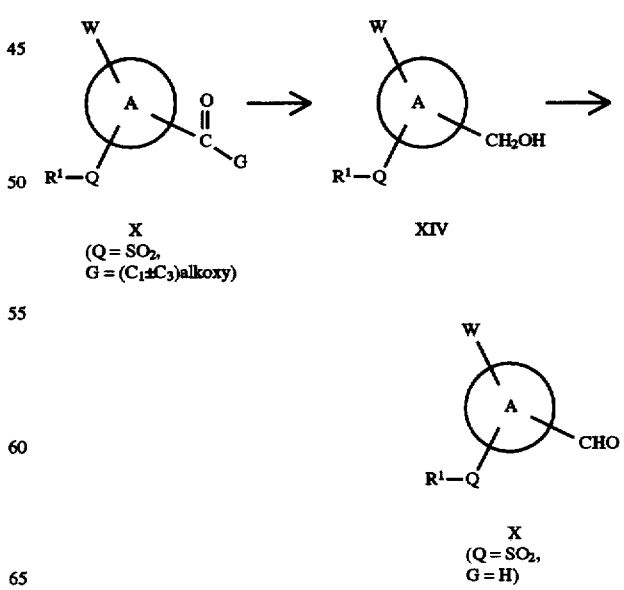

Scheme 4
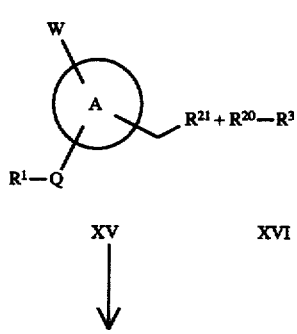
XV  XVI
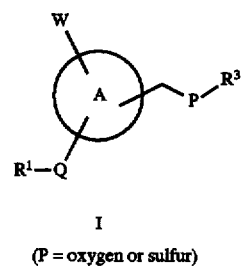
I
(P = oxygen or sulfur)
Scheme 5
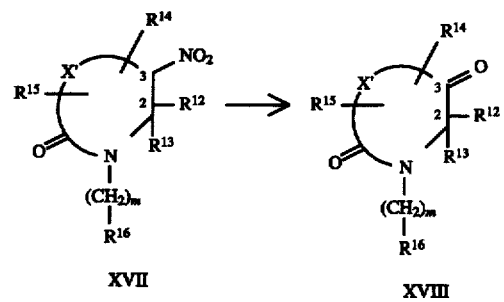
XVII  XVIII
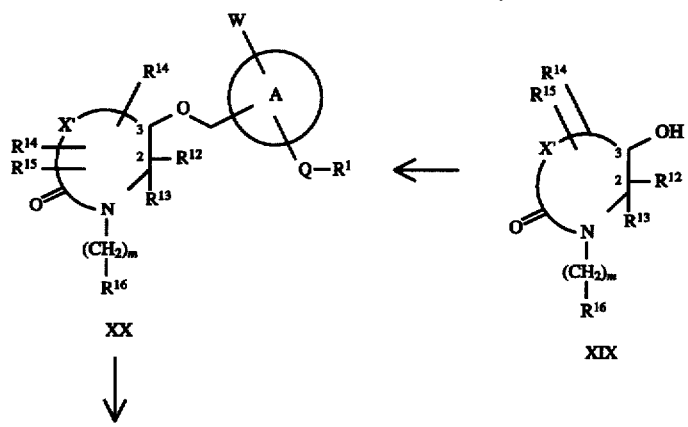
XX  XIX
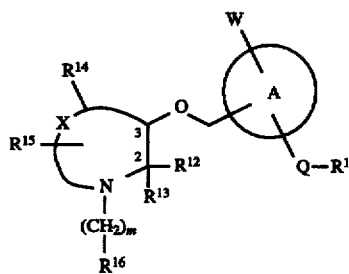
I
(P = O, R³ = VII)

Scheme 1 illustrates the preparation of compounds of the formula I wherein P is NR² from starting materials of the formula X wherein G is hydrogen, hydroxy, chloro, bromo or (C₁-C₆)alkoxy.

Referring to scheme 1, a compound of the formula X wherein G is hydrogen may be converted directly into the corresponding compound of the formula I by reacting it with a compound of the formula NH₂R³ in the presence of a reducing agent. Reducing agents that may be used include sodium cyanoborohydride, sodium triacetoxyborohydride, sodium borohydride, hydrogen and a metal catalyst, zinc and hydrochloric acid, and formic acid. This reaction is typically conducted in a reaction inert solvent at a temperature from about 0° C. to about 150° C. Suitable reaction inert solvents include lower alcohols (e.g., methanol, ethanol and isopropanol), 1,2-dichloroethane, acetic acid and tetrahydrofuran (THF). Preferably, the solvent is acetic acid, the temperature is about 25° C., the reducing agent is sodium triacetoxyborohydride, and the reaction is conducted in the presence of a dehydrating agent such as molecular sieves.

Alternatively, the reaction of a compound of the formula X with a compound of the formula NH₂R³ may be carried out in the presence of a dehydrating agent or using an apparatus designed to remove azeotropically the water generated, to produce an imine of the formula

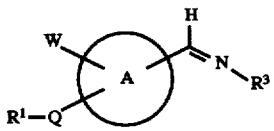

which is then reacted with a reducing agent as described above, preferably with sodium triacetoxyborohydride in an acetic acid or 1,2-dichloroethane solvent at about room temperature. The preparation of the imine is generally carried out in a reaction inert solvent such as benzene, xylene or toluene, preferably toluene, at a temperature from about 25° C. to about 110° C., preferably at about the reflux temperature of the solvent. Suitable dehydrating agents/ solvent systems include titanium tetrachloride/ dichloromethane titanium isopropoxide/dichloromethane and molecular sieves/THF. Titanium tetrachloride/ dichloromethane is preferred.

Compounds of the formula X wherein G is hydroxy, chloro, bromo or (C₁-C₆)alkoxy may be converted into the corresponding compounds of formula XII having the desired R³ group by reacting them with the appropriate compound of the formula NH₂R³ under conditions that will be obvious to those skilled in the art, and then reducing the resulting amides to yield the desired compounds having formula I wherein R² is hydrogen. When G is hydroxy, the compound of formula X is reacted with NH₂R³ in the presence of an activating agent. Appropriate activating agents include carbonyldiimidazole, diethylphosphoryl cyanide and dicyclohexylcarbodiimide. Carbonyldiimidazole is preferred. This reaction is generally conducted at a temperature from about 0° C. to about 50° C., preferably at about 25° C., in an inert solvent such as chloroform, diethyl ether, THF or dimethylformamide (DMF).

When G is chloro or bromo, the reaction of the compound of formula X with the appropriate compound of formula NH₂R³ is typically carried out in the presence of an acid scavenger in an aprotic solvent at a temperature from about 0° C. to about 100° C. Suitable acid scavengers include triethylamine (TEA), pyridine and inorganic salts such as sodium and potassium carbonate. Suitable solvents include methylene chloride (CH₂Cl₂), chloroform (CHCl₃), benzene, toluene and tetrahydrofuran (THF). Preferably, the reaction is conducted in CH₂Cl₂ at room temperature using TEA as the acid scavenger.

When G is O—(C₁-C₆)alkyl, the reaction of the compound of formula NH₂R³ is usually conducted in an aprotic solvent such as benzene, toluene, chlorobenzene or xylenes, at a temperature from about 25° C. to about 100° C., preferably at about the reflux temperature of the solvent.

Reduction of the compound of formula XII so formed yields the corresponding compound of the formula I wherein R² is hydrogen. This is generally accomplished using a reducing agent such as lithium aluminum hydride, borane dimethylsulfide complex or diborane, in an aprotic solvent such as THF, dioxane or diethyl ether, at a temperature from about 0° C. to about 70° C. Preferably, the reducing agent is borane dimethylsulfide complex and the reaction is carried out at about room temperature in an ethereal solvent such as THF.

Compounds of the formula I wherein R² is hydrogen may be converted into the corresponding compounds wherein R² is —CO₂(C₁-C₁₀)alkyl by reacting them with a (C₁-C₁₀) alkyl halo carbonate such as methyl or ethyl chloroformate in the presence of an acid scavenger. Typically, this reaction is conducted in a polar solvent such as chloroform, methylene chloride, water or a water/acetone mixture, at a temperature from about 0° C. to about 100° C., preferably at about room temperature. Suitable acid scavengers include triethylamine, pyridine and potassium and sodium carbonate or bicarbonate.

When R³ is a group of the formula II, the starting materials of the formula NH₂R³ may be prepared as described in U.S. patent application Ser. No. 566,338, filed Jul. 20, 1990. This application is incorporated herein in its entirety.

When R³ is a group of the formula III, the starting materials of the formula NH₂R³ may be prepared as described in U.S. patent application Ser. No. 532,525, filed Jun. 1, 1990 and PCT Patent Application PCT/US 91/02853, filed Apr. 25, 1991. Both these applications are incorporated herein in their entirety.

When R³ is a group of the formula IV, V or VI, the starting materials of the formula NH₂R³ may be prepared as described in U.S. patent application Ser. No. 557,442, filed Jul. 23, 1990 and PCT Patent Application PCT/US 91/03369, filed May 14, 1991. Both these applications are incorporated herein in their entirety.

When R³ is a group of the formula VII, the starting materials of the formula NH₂R³ may be prepared as described in U.S. patent application Ser. No. 724,268, filed Jul. 1, 1991, U.S. patent application Ser. No. 800,667, filed Nov. 27, 1991 and PCT Patent Application PCT/US 92/00065, filed Jan. 14, 1992. These applications are incorporated herein in their entirety.

When R³ is a group of the formula VIII, the starting materials of the formula NH₂R³ may be prepared as described in PCT Patent Application PCT/US 91/05776, filed Aug. 20, 1991, U.S. patent application Ser. No. 800, 667, filed Nov. 27, 1991 and PCT Patent Application PCT/ US 92/00065, filed Jan. 14, 1992. These applications are incorporated herein in their entirety.

When R³ is a group of the formula IX, the starting materials of the formula NH₂R³ may be prepared as described in U.S. patent application Ser. No. 719,884, filed Jun. 21, 1991. This application is incorporated herein in its entirety.

Scheme 2 illustrates the preparation of the starting materials of formula X wherein G is hydrogen and Q is other than $SO_2$. Once formed, these compounds can be converted into the corresponding compounds of the formula I or XI according to the procedures described above.

Referring to scheme 2, a compound of the formula XIII wherein Q is other than $SO_2$ is reacted with titanium tetrachloride ($TiCl_4$) and dichloromethyl methyl ether ($CHCl_2$—O—$CH_3$) at a temperature from about 0° C. to about room temperature in a methylene chloride solvent to yield the corresponding aldehyde of formula X wherein G is hydrogen. Alternatively, the compound of the formula XIII may be reacted with hexamethylene tetramine and trifluoroacetic acid at about 70° C. to yield the same product.

Those compounds of the formula X wherein Q is $SO_2$ may be obtained from their deoxygenated counterparts of the formula X wherein Q is —S— by reacting them with an oxidizing agent. For example, such oxidation may be carried out using metachloroperbenzoic acid in methylene chloride at about room temperature. It may also be carried out using peroxyphthalic acid magnesium hydrate in aqueous ethanol at a temperature from about 70° C. to about 100° C. The foregoing oxidation reactions can produce mixtures of the oxy and dioxy products (—SO— and —$SO_2$—) which can be separated by ordinary means.

Scheme 3 illustrates an alternate preparation of the starting materials of the formula X wherein G is hydrogen and Q is $SO_2$. Referring to scheme 3, a compound of formula X wherein Q is $SO_2$ and G is ($C_1$–$C_3$)alkoxy is reacted with a reducing agent in a reaction inert solvent, for example lithium borohydride ($LiBH_4$) in tetrahydrofuran (THF). The reduction, which yields an alcohol of the formula XIV, is usually conducted at a temperature from about 0° C. to about 100° C., preferably by heating the reaction mixture to the reflux temperature of the solvent. The alcohol of formula XIV may then be oxidized using methods known to those skilled in the art. For example, treatment of a solution of such alcohol in a solvent such as methylene chloride with an oxidizing agent such as pyridinium dichromate at a temperature from about 0° C. to about 50° C., preferably at room temperature, will yield the corresponding compounds of formula X wherein G is hydrogen and Q is $SO_2$. Other oxidizing agents/solvent systems such as manganese dioxide/acetone and chromium trioxide/acetic anhydride/acetic acid are also capable of producing this conversion.

Compounds of the formula I wherein P is O or S may be prepared as described below and illustrated in Scheme 4. Referring to Scheme 4, a compound of the formula XV is reacted with a compound of the formula $R^{20}$–$R^3$ in the presence of a base to form the corresponding compound of formula I. One of $R^{20}$ and $R^{21}$ is PH, wherein P is O or S, and the other is a suitable leaving group such as chlorine, bromine, iodine, mesylate or tosylate. This reaction is generally conducted in a reaction inert solvent, such as an ether (e.g., diethyl ether, tetrahydrofuran, dimethoxyethane, dioxane), dialkyl amide (e.g., dimethylformamide or dimethylacetamide) or dimethylsulfoxide, at a temperature range from about −5° C. to about 100° C. The reaction may be performed at from one to about three atmospheres of pressure, although it is normally done at atmospheric pressure. Suitable bases include alkali metal amides or hydrides, such as sodium amide, potassium bis(trimethylsilyl)amide or potassium hydride, or alkali metal alkoxides such as sodium methoxide. Preferably, the reaction is carried out in dimethoxyethane in the presence of potassium bis (trimethylsilyl)amide at about 25° C.

Compounds of the formula XV wherein $R^{21}$ is a leaving group may be prepared using procedures familiar to those skilled in the art. For example, such a compound wherein $R^{21}$ is mesylate may be prepared by reacting a compound of the formula XIV, as depicted in Scheme 3, with methanesulfonyl chloride in methylene chloride in the presence of triethylamine at about 0° C.

Compounds of the formula $R^{20}$–$R^3$ wherein $R^{20}$ is OH may be prepared from the corresponding ketones via reduction, using any of a variety of reducing agents such as sodium borohydride in methanol or lithium aluminum hydride in a suitable inert solvent such as diethyl ether or tetrahydrofuran. The corresponding cis and trans isomeric alcohols may be prepared using selective reducing agents to obtain the desired isomer, or by selective oxidation of the racemic alcohol followed by isolation of the desired isomer. Such procedures are described in European Patent Application EP 0 499 313 A1, which was published on Aug. 19, 1992. The foregoing application is incorporated herein by reference in its entirety.

The ketone intermediates used in the foregoing process may be prepared by methods known in the art from commercially available starting materials or by minor variations of such methods that will be obvious to those skilled in the art. Such ketone intermediates wherein $R^3$ is a group of the formula IV, V or VI may be prepared as described in World Patent Application WO 92/01688, which was published on Feb. 6, 1992. This application is incorporated herein by reference in its entirety. Such ketone intermediates wherein $R^3$ is a group of the formula II, III or IX may be prepared as described in U.S. Pat. No. 5,162,339, which issued on Nov. 10, 1992. This patent is also incorporated herein by reference in its entirety.

Compounds of the formula $R^{20}$–$R^3$ wherein $R^{20}$ is OH may also be prepared from the corresponding compounds of the formula

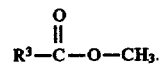

(The latter compounds may be prepared, for example, when $R^3$ is a group of the formula VII or VIII, as described by Desai et al. in *J. Med. Chem.*, 35, 4911–4913 (1992) and in U.S. Pat. No. 5,232,929, which issued on Aug. 3, 1993. Both these references are incorporated herein by reference in their entirety).

First, the ring nitrogen of the compound of formula

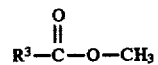

is blocked with a suitable protecting group, e.g., carbonylbenzyloxy (CBZ), as described in U.S. Pat. No. 5,232,929. The resulting compound is then hydrolysed using 10% potassium hydroxide or sodium hydroxide in methanol/water, or 1M lithium hydroperoxide in tetrahydrofuran (THF)/water, at a temperature from about room temperature to about 100° C.

The above reaction produces a carboxylic acid of the formula $R^3COOH$. The acid is then heated in benzene at about the reflux temperature in the presence of lead tetraacetate and cuptic acetate, to produce a compound of the formula

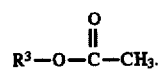

Variations of this reaction, which involves the conversion of a carboxylic acid to an acetate, are described in Corey et al., J. Amer. Chem. Soc., 85, 165–169 (1963). Hydrolysis of the resulting compound of the formula

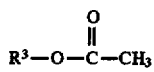

according to the procedure described above for the hydrolysis of compounds of the formula

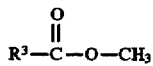

yields the desired intermediate of the formula $R^{20}-R^3$ wherein $R^{20}$ is hydroxy.

The protecting group (e.g., CBZ) can be removed at a later stage in the synthesis using methods described in the literature, e.g., hydrogenation in the presence of a palladium on carbon catalyst in ethanol or ethyl acetate at a pressure of from about one to three atmospheres and a temperature from about 25° C. to about 50° C.

The foregoing method for preparing compounds of the formula $R^{20}-R^3$ is preferred for such compounds wherein $R^3$ is a group of the formula VII or VIII.

Compounds of the formula $R^{20}-R^3$ wherein $R^{20}$ is SH may be prepared from the corresponding compounds wherein $R^{20}$ is OH by treating the latter with phosphorus pentasulfide or Lawesson's reagent [2,4-bis(4-methoxyphenyl)-1,3-dithia-2,4-diphosphetane-2,4-disulfide] in a suitable inert solvent such as pyridine, at a temperature between about room temperature and the 120° C.

Alternatively, alcohols of the formula HO—$R^3$ may be converted to the corresponding thiol esters, which may be subsequently converted to thiols of the formula $R^3$SH according to the procedure of R. P. Volante, *Tetrahedron Letters*, 22 (33), 3119–3122 (1981).

Compounds of the formula I wherein $R^3$ is a group of the formula VII or VIII and P is oxygen may also be prepared by the procedure depicted in scheme 5 and described below. Referring to scheme 5, a compound of the formula XVII, wherein X' is defined as X in formula I except that it has one less carbon atom in the $(CH_2)_q$ chain, is converted into the corresponding 3-oxo compound of formula XVIII. This can be accomplished, as exemplified in Example 11, by reacting the compound of formula XVIII with an alkali metal alkoxide such as potassium tert-butoxide in an inert solvent such as dichloromethane/methanol at about room temperature, cooling the reaction mixture to about −78° C., treating the mixture with ozone for approximately one hour, and then bubbling nitrogen gas through the mixture to remove the excess ozone.

Reduction of the resulting compound of formula XVIII with sodium borohydride in methanol yields the corresponding hydroxy derivative of formula XIX. Appropriate reducing agents include potassium borohydride and sodium borohydride. The reaction is usually carried out in a methanol or ethanol solvent at a temperature from about −5° C. to about 100° C., preferably at about 25° C. Alternatively, the ketone of formula XVIII can be converted into the corresponding alcohol of formula XIX using an aluminum alkoxide, preferably aluminum isopropoxide, in an alcohol solvent, preferably isopropanol, at a temperature from about 20° C. to about 125° C., preferably at the boiling point of the solvent.

Compounds of the formula XX are then formed by reacting the corresponding compounds of the formula XIX with a compound of the formula XV, as depicted in scheme 4 and wherein $R^{21}$ is a suitable leaving group such as chlorine, bromine, iodine, mesylate or tosylate. The reaction is carried out as described above for preparing compounds of the formula I wherein P is oxygen or sulfur from compounds of the formula XV.

Reduction of the oxo group of the resulting compounds of formula XX yields the corresponding compounds of formula I wherein $R^3$ is a group of the formula VII or VIII. Examples of suitable reducing agents are lithium aluminum hydride, borane dimethylsulfide in THF, borane in THF and sodium borohydride-titanium (IV) chloride. Best results are obtained using borane dimethylsulfide in THF. The reaction may be carried out at temperatures from about room temperature to about 150° C., and is preferably carried out at the reflux temperature of the solvent.

Compounds of the formula I where P is SO or $SO_2$ may be prepared from the compounds of formula I where P is S by methods well known to those skilled in the art using oxidizing reagents such as metachloroperbenzoic acid or potassium peroxymonosulfate, as described in the literature.

The preparation of other compounds of the formula I not specifically described in the foregoing experimental section can be accomplished using combinations of the reactions described above that will be apparent to those skilled in the art.

In each of the reactions discussed or illustrated in schemes 1 to 5 above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The novel compounds of the formula I and the pharmaceutically acceptable salts thereof are useful as substance P antagonists, i.e., they possess the ability to antagonize the effects of substance P at its receptor site in mammals, and therefore they are able to function as therapeutic agents in the treatment of the aforementioned disorders and diseases in an afflicted mammal.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds of the formula I which are also acidic in nature, e.g., where $R^6$ or $R^{10}$ is carboxyphenyl, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of formula I and their pharmaceutically acceptable salts exhibit substance P receptor-binding activity and therefore are of value in the treatment and prevention of a wide variety of clinical conditions the treatment or prevention of which are effected or facilitated by a decrease in substance P mediated neurotransmission. Such conditions include inflammatory diseases (e.g., arthritis, psoriasis, asthma and inflammatory bowel disease), anxiety, depression or dysthymic disorders, urinary incontinence, gastrointestinal disorders such as emesis and colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P antagonists for the control and/or treatment of any of the aforesaid clinical conditions in mammals, including humans.

The compounds of the formula I and the pharmaceutically acceptable salts thereof can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the formula I and their pharmaceutically acceptable salts ("the therapeutic compounds") may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the therapeutic compounds of the present invention as substance P receptor antagonists may be determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a −70° C. freezer and homogenized in 50 volumes (w./v.) of an ice-cold 50 mM Tris (i.e., trimethamine which is 2-amino-2-hydroxymethyl-1,3-propanediol)hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 4 µg/ml of bacitracin, 4 µg/ml of leupeptin, 2 µg of chymostatin and 200 g/ml of bovine serum albumin. This step completes the production of the tissue preparation.

The radioligand binding procedure is then carried out in the following manner, viz., by initiating the reaction via the addition of 100 µl of the test compound made up to a concentration of 1 µM, followed by the addition of 100 µl of radioactive ligand made up to a final concentration 0.5 mM and then finally by the addition of 800 µl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The ability of the therapeutic compounds of this invention to inhibit substance P induced effects in vivo may be determined by the following procedures "a" through "d". (Procedures "a" through "c" are described in Nagahisa et al., *European Journal of Pharmacology*, 217, 191–5 (1992), which is incorporated herein by reference in its entirety.)

a. Plasma extravasation in the skin

Plasma extravasation is induced by intradermal administration of substance P (50 µl, 0.01% BSA-saline solution) in dorsal skin of pentobarbital (25 mg/kg i.p.) anesthetized male Hartley guinea pigs weighing 450–500 g. The compound to be tested is dissolved in 0.1% methyl cellulose-water (MC) and dosed p.o. 1 hour before substance P challenge (3 pmol/site). Evans blue dye (30 mg/kg) is administered intravenously 5 minutes before challenge. After 10 minutes, the animals are sacrificed, the dorsal skin is removed, and the blue spots are punched out using a cork borer (11.5 mm oral dose (o.d.)). Tissue dye content is quantitated after overnight formamide extraction at 600 nm absorbance.

b. Capsaicin-induced plasma extravasation

Plasma extravasation is induced by intraperitoneal injection of capsaicin (10 ml of 30 µM solution in 0.1% BSA/saline) into pentobarbital anesthetized (25 mg/kg i.p.) guinea pigs. The compound to be tested is dissolved in 0.1% MC and dosed p.o. 1 hour before capsaicin challenge. Evans blue dye (30 mg/kg) is administered i.v. 5 minutes before challenge. After 10 minutes, the animals are sacrificed, and both right and left ureters are removed. Tissue dye content is quantitated as in "a" above.

c. Acetic acid-induced abdominal stretching

Male ddY mice (SLC, Japan), weighing 14–18 g, were fasted overnight. The compound to be tested is dissolved in 0.1% MC and dosed p.o. 0.5 hour before acetic acid (AA) injection (0.7%, 0.16 ml/10 g body weight). The animals are placed in clear beakers (1 per beaker) and the stretching response is counted 10 to 20 minutes after the AA injection (10 minute interval).

d. Substance P-induced hyperlocomotor paradigm

The anti-psychotic activity of the therapeutic compounds of the present invention as neuroleptic agents for the control of various psychotic disorders may be determined by a study of their ability to suppress substance P-induced or substance P agonist induced hypermotility in guinea pigs. This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The present invention is illustrated by the following examples. It will be understood, however, that the invention is not limited to the specific details of these examples.

PREPARATION 1

2-Methoxy-5-[N-methyl-N-(2,4-dimethyl-5-thiazolesulfonyl)amino]benzaldehyde

A. N-(4-Methoxyphenyl)-N,2,4-trimethylthiazole-5-sulfonamide

Under nitrogen in a flame-dried round-bottomed flask fitted with a dropping funnel, stir bar and condensor, was added N-methyl-p-anisidine (1.0 grams, 7.29 mmol) in 30 mL of anhydrous tetrahydrofuran (THF). To this was added triethylamine (1.01 mL, 7.29 mmol) and the flask was cooled to 0° C. with an ice bath. Next, 2,4-dimethyl-5-thiazolesulfonyl chloride (1.54 grams, 7.29 mmol, Maybridge Chem. Co.) in 20 mL of THF was added dropwise and the reaction allowed to stir at 25° C. overnight. The reaction was quenched by pouring it slowly into 200 mL of saturated aqueous sodium bicarbonate and extracting the crude product with dichloromethane ($CH_2Cl_2$). After drying the organic extracts over magnesium sulfate ($MgSO_4$), the solvent was removed in vacuo to a dark brown oil. Chromatography on silica gel, eluting with hexanes:ethyl acetate (EtOAc) (4:1), gave 380 mg of pale brown oil.

Mass spectrum (%): m/e 312 (12, M+), 136 (100).

$^1$H NMR ($CDCl_3$) δ 2.2 (s, 3H), 2.7 (s, 3H), 3.3 (s, 3H), 3.8 (s, 3H), 6.8 (m, 2H), 7.1 (m, 2H).

B. 2-Methoxy-5-[N-methyl-N-(2,4-dimethyl-5-thiazolesulfonyl)amino]benzaldehyde

To a flame-dried round-bottomed flask with a nitrogen inlet and stir bar was added the preceding intermediate from step "A" (0.20 g, 0.7 mmol) and 20 mL of anhydrous $CH_2Cl_2$. After cooling to 0° C., titanium chloride (0.33 mL, 3 mmol) was added dropwise and the reaction was stirred at 0° C. for 30 min. Dichloromethyl methyl ether (0.14 mL, 1.56 mmol) was then added via syringe and the reaction stirred at 0° C. for another 3 hours, then at room temperature for a further 18 hours, at which time thin-layer chromatography (tlc) showed no starting material remaining. The reaction was quenched by pouring it into 200 mL of saturated aqueous sodium bicarbonate ($NaHCO_3$), stirring for 30 min and extracting with $CH_2Cl_2$. The extracts were dried ($MgSO_4$) and concentrated in vacuo to an oil. Chromatography on silica gel eluting with hexanes:EtOAc (3:2) gave the title product as a yellow oil, 70 mg (29%).

Mass spectrum (%) m/e 340 (10, M+), 164 (100).

$^1$H NMR ($CDCl_3$) δ 2.1 (s, 3H), 2.5 (s, 3H), 3.1 (s, 3H), 3.9 (s, 3H), 7.0 (d, 1H), 7.5 (m, 1H), 7.6 (m, 1H), 10.4 (s, 1H).

The following intermediate aldehydes of the general formula X were prepared by a procedure similar to that described in Preparation 1.

PREPARATION 2

2-Methoxy-5-[N-(4,5-dimethyl-2-thiazolyl)-N-methanesulfonyl)amino]benzaldehyde

Waxy solid, 39% yield.

MS: m/e 340 (M+, 20%), 261 (65%).

PREPARATION 3

2-Methoxy-5-[N-(4,5-dimethyl-2-thiazolyl)-N-methyl]aminobenzaldehyde

Oil, 7% yield.

MS: m/e 277 ($M^{+1}$, 20%), 276 (100%), 126 (30).

$^1$H NMR (CDCl$_3$) δ 2.1 (d, 6H), 3.4 (s, 3H), 4.0 (s, 3H), 7.0 (d, 1H), 7.6 (q, 1H), 7.8 (d, 1H), 10.5 (s, 1H).

PREPARATION 4

2-Methoxy-5-[N-(4,5-dimethyl-2-thiazolyl)]aminobenzaldehyde

Mp 137°–139° C., 20% yield.

MS: m/e 262 (M+, 100%).

$^1$H NMR (CDCl$_3$) δ 2.15 (s, 3H), 2.25 (s, 3H), 3.9 (s, 3H), 7.0 (d, 1H), 7.6 (dd, 1H), 7.7 (dd, 1H), 10.5 (s, 1H).

PREPARATION 5

2-Isopropoxy-5-[N-methyl-N-(2,4-dimethyl-5-thiazolesulfonyl)amino]benzaldehyde

Oil, 34% yield.

$^1$H NMR (CDCl$_3$) δ 1.4 (d, 6H), 2.20 (s, 3H), 2.6 (s, 3H), 3.25 (s, 3H), 4.70 (m, 1H), 6.95 (d, 1H), 7.45 (d, 1H), 7.55 (dd, 1H), 10.4 (s, 1H).

PREPARATION 6

2-Isopropoxy-5-[N-isobutyl-N-(2,4-dimethyl-5-thiazolesulfonyl)amino]benzaldehyde Oil, 54% yield.

MS: m/e 411 ($M^{+1}$, 100), 412 ($M^{+2}$, 30), 236.

$^1$H NMR (CDCl$_3$) δ 0.9 (d, 6H), 1.45 (d, 6H), 1.6 (m, 1H), 2.2 (s, 3H), 2.7 (s, 3H), 3.4 (d, 2H), 4.7 (m, 1H), 7.0 (d, 1H), 7.5 (m, 2H), 10.4 (s, 1H).

PREPARATION 7

2-Methoxy-5-[N-isobutyl-N-(2,4-dimethyl-5-thiazolesulfonyl)amino]benzaldehyde

Oil, 96% yield.

MS: m/e 383 ($M^{+1}$, 100), 384 ($M^{+2}$, 30), 208.

$^1$H NMR (CDCl$_3$) δ 1.0 (d, 6H), 1.6 (m, 1H), 2.2 (s, 3H), 2.6 (s, 3H), 3.4 (d, 2H), 3.9 (s, 3H), 7.0 (d, 1H), 7.5 (m, 2H), 10.4 (s, 1H).

PREPARATION 8

2-Methoxy-5-[N-isopropyl-N-(2,4-dimethyl-5-thiazolesulfonyl)amino]benzaldehyde

Oil, 48% yield.

MS: m/e 369 ($M^{+1}$, 100), 194 (30).

$^1$H NMR (CDCl$_3$) δ 1.1 (d, 6H), 2.35 (s, 3H), 2.65 (s, 3H), 3.9 (s, 3H), 4.5 (m, 1H), 7.0 (d, 1H), 7.4 (m, 1H), 7.5 (d, 1H), 10.4 (s, 1H).

PREPARATION 9

2-Isopropoxy-5-[N-isopropyl-N-(2,4-dimethyl-5-thiazolesulfonyl)amino]benzaldehyde Oil, 52% yield.

MS: m/e 397 ($M^{+1}$, 100), 398 ($M^{+2}$, 30), 222 (45).

$^1$H NMR (CDCl$_3$) δ 1.1 (d, 6H), 1.4 (d, 6H), 1.4 (d, 6H), 2.4 (m, 3H), 2.6 (m, 3H), 4.5 (m, 1H), 4.7 (m, 1H), 7.0 (d, 1H), 7.4 (q, 1H), 7.5 (d, 1H), 10.4 (s, 1H).

PREPARATION 10

2-Trifluoromethoxy-5-[N-(4,5-dimethyl-2-thiazolyl)-N-methanesulfonyl)amino]benzaldehyde Oil.

$^1$H NMR (CDCl$_3$) δ 2.3 (s, 3H), 2.7 (s, 3H), 3.4 (s, 3H), 7.4 (d, 1H), 7.6 (d, 1H), 7.8 (dd, 1H), 10.3 (s, 1H).

EXAMPLE 1

2,4-Dimethylthiazole-5-sulfonic acid [4-methoxy-3-((2S,3S)-2-phenylpiperidin-3-ylaminomethyl)phenyl]-methylamide dihydrochloride hemihydrate To a flame-dried round-bottomed flask fitted with a Dean-Stark trap, condensor, nitrogen inlet and a stir bar, the title compound of Preparation 1 (70 mg, 0.21 mmol) in 5 mL of anhydrous toluene was added to (+)-(2S,3S)-3-amino-2-phenylpiperidine (36 mg, 0.21 mmol). The mixture was refluxed for approximately 3 hours, the solvent was removed in vacuo and the residue was dissolved in 5 mL of 1,2-dichloroethane. Sodium triacetoxyborohydride (62 mg, 0.29 mmol) was added and the reaction stirred at 25° C. overnight. The solvent was next removed in vacuo, the residue was treated with 10 mL of water and extracted 4×20 mL with CH$_2$Cl$_2$. The organic extracts were dried (MgSO$_4$) and concentrated in vacuo to a yellow oil. Chromatography on silica gel eluting with CH$_2$Cl$_2$:CH$_3$OH: concentrated NH$_4$OH (97:2:1) gave the free base as a clear oil, 37 mg. This was converted to the hydrochloride salt in the usual manner (dissolved the free base in ethyl ether (Et$_2$O) and treated with hydrogen chloride gas, concentrated in vacuo, and recrystallized the crude salt from CH$_3$OH:Et$_2$O) to give a white salt, 31 mg (24%), m.p. 260°–264° C.

Anal. calc'd for C$_{25}$H$_{32}$N$_4$O$_3$S•2HCl•1/2H$_2$O: C, 51.54; H, 6.06; N, 9.62. Found: C, 51.31; H, 5.79; N, 9.76.

$^1$H NMR (CDCl$_3$, free base) δ 1.3–2.0 (m, 5H), 2.05 (d, 1H), 2.15 (s, 3H), 2.7 (s, 3H), 2.8 (m, 2H), 3.15 (s, 3H), 3.25 (d, 1H), 3.35 (d, 1H), 3.45 (s, 3H), 3.6 (d, 1H), 3.85 (d, 1H), 6.55 (d, 1H), 6.8 (d, 1H), 6.95 (dd, 1H), 7.25 (m, 5H).

The title compounds of Examples 2–10 were prepared by a procedure similar to that of Example 1.

EXAMPLE 2

N-(4,5-Dimethylthiazol-2-yl)-N-[4-methoxy-3-((2S,3S)-2-phenylpiperidin-3-ylaminomethyl)phenyl]-methanesulfonamide dihydrochloride hemihydrate 40% yield, mp 247°–249° C.

MS: m/e 501 ($M^{+1}$), 421, 381, 247 (100%).

$^1$H NMR (CDCl$_3$, free base) δ 1.4 (d, 1H), 1.6 (t, 1H), 1.75 (m, 2H), 1.9 (m, 1H), 2.15 (d, 1H), 2.3 (m, 6H), 2.85 (m, 2H), 3.25 (d, 1H), 3.35 (d+s, 4H), 3.55 (s, 3H), 3.7 (d, 1H), 3.9 (d, 1H), 6.7 (d, 1H), 7.15 (d, 1H), 7.25 (m, 6H).

Anal. calc'd for C$_{25}$H$_{32}$N$_4$O$_3$S$_2$•2HCl•1/2H$_2$O: C, 51.54; H, 6.06; N, 9.62. Found: C, 51.87; H, 5.81; N, 9.55.

EXAMPLE 3

{5-[(4,5-Dimethylthiazol-2-yl)methylamino]-2-methoxybenzyl}-((2S,3S)-2-phenylpiperidin-3-yl)amine trihydrochloride hydrate 26% yield, mp 220°–225° C.

MS: m/e 436 (M+, 16%), 317 (45%), 262 (100%).

¹H NMR (CDCl₃, free base), δ 1.5 (m, 1H), 1.6 (m, 1H), 1.9 (m, 1H), 2.1 (s, 3H), 2.2 (s, 3H), 2.8 (m, 2H), 3.2 (m, 1H), 3.3 (s, 3H), 3.4 (d, 1H), 3.5 (s, 3H), 3.6 (d, 1H), 3.9 (d, 1H), 6.4 (d, 1H), 6.9 (d, 1H), 7.1 (q, 1H), 7.4 (m, 5H).

Anal. calc'd for $C_{25}H_{32}N_4OS \cdot 3HCl \cdot 3/2H_2O$: C, 52.40; H, 6.68; N, 9.78. Found: C, 52.12; H, 6.64; N, 9.55.

EXAMPLE 4

{5-(4,5-Dimethylthiazol-2-ylamino)-2-methoxybenzyl}-(2S,3S)-2-phenylpiperidin-3-ylamine trihydrochloride 28% yield, mp 272°–275° C.

MS: m/e 422 (M+, 40%), 303 (54%), 248 (100%).

¹H NMR (CDCl₃, free base) δ 1.35–2.15 (m, 7H), 2.18 (s, 3H), 2.23 (s, 3H), 2.8 (m, 2H), 3.28 (d, 1H), 3.4 (d, 1H), 3.5 (s, 3H), 3.65 (d, 1H), 3.9 (d, 1H), 6.65 (d, 1H), 6.75 (d, 1H), 7.15 (dd, 1H), 7.3 (m, 5H).

Anal. calc'd for $C_{24}H_{30}N_4OS \cdot 3HCl$: C, 54.19; H, 6.25; N, 10.53. Found: C, 53.91; H, 6.39; N, 10.27.

EXAMPLE 5

4,5-Dimethylthiazole-2-sulfonic acid methyl-[3-((2S,3S)-2-phenylpiperidin-3-ylaminomethyl)-4-trifluoromethoxyphenyl]-amide trihydrochloride hydrate 12% yield, mp 239°–240° C. (dec.).

MS: m/e 555 (M⁺¹), 380.

¹H NMR (CDCl₃, free base) δ 1.5 (m, 1H), 1.7 (m, 1H), 1.9 (m, 4H), 2.1 (m, 1H), 2.2 (s, 3H), 2.7 (s, 3H), 2.8 (m, 2H), 3.2 (s, 3H), 3.3 (m, 1H), 3.5 (q, 2H), 3.9 (d, 1H), 7.0 (m, 3H), 7.2 (m, 5H).

Anal. calc'd for $C_{25}H_{29}F_3N_4O_3S_2 \cdot 3HCl \cdot H_2O$: C, 44.09; H, 4.88; N, 8.23. Found: C, 44.36; H, 4.95; N, 8.51.

EXAMPLE 6

2,4-Dimethylthiazole-5-sulfonic acid [4-isopropoxy-3-((2S,3S)-2-phenylpiperidin-3-ylaminomethyl)phenyl]-methylamide dihydrochloride 10% yield, mp 227°–230° C.

MS: m/e 529 (M⁺¹, 100), 354.

¹H NMR (CDCl₃, free base) δ 1.05 (dd, 6H), 1.35–2.10 (m, 6H), 2.15 (s, 3H), 2.70 (s, 3H), 2.85 (m, 2H), 3.15 (s, 3H), 3.30 (d, 1H), 3.45 (m, 2H), 3.85 (d, 1H), 4.30 (m, 1H), 6.65 (d, 1H), 6.83 (d, 1H), 6.95 (dd, 1H), 7.3 (m, 5H).

Anal. calc'd for $C_{27}H_{36}N_4O_3S_2 \cdot 2HCl$: C, 53.90; H, 6.37; N, 9.31. Found: C, 54.55; H, 6.29; N, 9.33.

EXAMPLE 7

2,4-Dimethylthiazole-5-sulfonic acid [4-isopropoxy-3-((2S,3S)-2-phenylpiperidin-3-ylaminomethyl)phenyl]-isopropylamide dihydrochloride 24% yield, mp 250°–254° C.

MS: m/e 557 (M⁺¹, 100), 398, 382 (100).

¹H NMR (CDCl₃, free base) δ 1.0–1.15 (m, 12H), 1.4 (d, 1H), 1.5–1.95 (m, 4H), 2.05 (d, 1H), 2.30 (s, 3H), 2.65 (s, 3H), 2.8 (m, 2H), 3.25 (m, 2H), 3.55 (d, 1H), 3.85 (d, 1H), 4.3 (m, 1H), 4.6 (m, 1H), 6.6 (d, 1H), 6.8 (d, 1H), 6.85 (dd, 1H), 7.25 (m, 5H).

Anal. calc'd for $C_{29}H_{40}N_4O_3S_2 \cdot 2HCl$: C, 55.31; H, 6.72; N, 8.90. Found: C, 55.55; H, 6.51; N, 8.64.

EXAMPLE 8

2,4-Dimethylthiazole-5-sulfonic acid [4-methoxy-3-((2S,3S)-2-phenylpiperidin-3-ylaminomethyl)phenyl]-isopropylamide dihydrochloride 15% yield, mp 240°–242° C.

MS: m/e 530 (M⁺², 100), 371, 355 (100).

¹H NMR (CDCl₃, free base) δ 1.05 (d, 6H), 1.4 (d, 1H), 1.55–1.95 (m, 4H), 2.05 (d, 1H), 2.35 (s, 3H), 2.70 (s, 3H), 2.80 (m, 2H), 3.25 (m+d, 2H), 3.45 (s, 3H), 3.65 (d, 1H), 3.85 (d, 1H), 4.6 (m, 1H), 6.6 (d, 1H), 6.8 (d, 1H), 6.9 (dd, 1H), 7.25 (m, 5H).

Anal. calc'd for $C_{27}H_{36}N_4O_3S_2 \cdot 2HCl$: C, 53.90; H, 6.37; N, 8.32. Found: C, 53.73; H, 6.30; N, 8.44.

EXAMPLE 9

2,4-Dimethylthiazole-5-sulfonic acid [4-methoxy-3-((2S,3S)-2-phenylpiperidin-3-ylaminomethyl)phenyl]-isobutylamide dihydrochloride hydrate 16% yield, mp 225°–230° C.

MS: m/e 544 (M⁺², 70), 385, 369 (100).

¹H NMR (CDCl₃, free base) δ 0.9 (d, 6H), 1.4 (d, 1H), 1.5–1.95 (m, 6H), 2.05 (d, 1H), 2.15 (s, 3H), 2.70 (s, 3H), 2.8 (m, 1H), 3.25 (m, 3H), 3.35 (d, 1H), 3.45 (s, 3H), 3.6 (d, 1H), 3.85 (d, 1H), 6.6 (d, 1H), 6.8 (d, 1H), 6.9 (dd, 1H), 7.25 (m, 5H).

Anal. calc'd for $C_{28}H_{38}N_4O_3S_2 \cdot 2HCl \cdot H_2O$: C, 53.07; H, 6.68; N, 8.84. Found: C, 52.88; H, 6.38; N, 8.85.

EXAMPLE 10

2,4-Dimethylthiazole-5-sulfonic acid [4-isopropoxy-3-((2S,3S)-2-phenylpiperidin-3-ylaminomethyl)phenyl]-isobutylamide dihydrochloride 5% yield, mp 150°–160° C.

MS: m/e 572 (M⁺², 100), 570 (M+), 397.

¹H NMR (CDCl₃, free base) δ 0.9 (d, 6H), 1.02 (d, 3H), 1.12 (d, 3H), 1.35–2.10 (m+s, 8H), 2.7 (s, 3H), 2.8 (m, 2H), 3.2–3.55 (m+d, 5H), 3.85 (d, 1H), 4.3 (m, 1H), 6.6 (d, 1H), 6.8 (d, 1H), 6.9 (dd, 1H), 7.25 (m, 5H).

Anal. calc'd for $C_{30}H_{42}N_4O_3S_2 \cdot 2HCl \cdot Et_2O$: C, 57.05; H, 7.32; N, 7.83. Found: C, 57.41; H, 6.89; N, 8.25.

EXAMPLE 11

6-Phenylpiperidine 2-5-dione

To a stirred solution of 5-nitro-2-oxo-6-phenylpiperidine (20 g, 90.8 mmol) in 320 mL of dichloromethane and 320 mL of methanol, potassium tert-butoxide (10.19 g, 90.8 mmol) was added in portions over one minute. After stirring for 15 minutes at 25° C., the solution was cooled to −78° C. and treated with ozone for approximately one hour to produce a blue solution. The solution was then treated with nitrogen gas for 15 minutes to remove excess ozone. Dimethylsulfide (12 mL, 163 mmol) was added and the reaction was allowed to warm to room temperature. Removal of the solvent in vacuo provided a yellow residue which was filtered, washed with dichloromethane and diethyl ether and dried to a white solid, 12.1 g (70%).

¹H NMR (CDCl₃): δ 2.6–2.8 (m, 4H), 5.0 (s, 1H), 6.7 (bs, 1H), 7.4 (s, 5H).

I claim:

1. A compound of the formula

[structure diagram]

or a pharmaceutically acceptable salt thereof, wherein:

Q is —NH—, —N($C_1$–$C_6$ alkyl)-, or —$SO_2$N($C_1$–$C_6$ alkyl)-, wherein the foregoing —$SO_2$N($C_1$–$C_6$ alkyl)- moiety attaches to the phenyl group through the nitrogen atom and attaches to $R^1$ through the sulfur atom;

W is hydrogen, $C_1$–$C_6$ alkyl, —S($C_1$–$C_3$ alkyl), halo or $C_1$–$C_6$ alkoxy, wherein the alkyl moieties of the foregoing W groups are optionally substituted with 1 to 3 fluoro substituents;

$R^1$ is a heteroaryl group selected from the group consisting of thiazolyoxazolyllyl, thienyl, triazolyl, oxazolyl, oxadiazolyl, thiadiazolyl, imidazolyl, pyridinyl, and pyrimidinyl, wherein said heteroaryl groups are optionally substituted with 1 to 3 substituents independently selected from phenyl, $C_1$–$C_6$ alkyl, halo, and $C_1$–$C_6$ alkoxy wherein the alkyl moieties of said optional substituents are optionally substituted with 1 to 3 fluoro substituents;

$R^3$ is group of the formula VII

[structure diagram] VII wherein X is $(CH_2)_q$ wherein q is an integer ranging from 1 to 6, and m is an integer ranging from 0 to 8;

$R^{12}$ is hydrogen, $C_1$–$C_6$ alkyl, $C_3$–$C_7$ cycloalkyl; aryl selected from biphenyl, phenyl, indanyl, and naphthyl; heteroaryl selected from thienyl, furyl, pyridyl, thiazolyl, isothiazolyl, oxazolyl, isoxazolyl, triazolyl, tetrazolyl, and quinolyl; benzhydryl or —($C_1$–$C_6$ alkyl)-(phenyl), wherein the foregoing aryl and heteroaryl groups and the phenyl moieties of said (phenyl)$C_1$–$C_6$ alkyl and benzhydryl groups are optionally substituted with 1 to 3 substituents independently selected from halo, nitro, $C_1$–$C_{10}$ alkyl, $C_1$–$C_{10}$ alkoxy, amino, ($C_1$–$C_6$ alkoxy)$C_1$–$C_6$ alkyl, —NH($C_1$–$C_6$ alkyl), —C(O)O($C_1$–$C_6$ alkyl), —($C_1$–$C_6$ alkyl)C(O)($C_1$–$C_6$ alkyl), —OC(O)($C_1$–$C_6$ alkyl), —($C_1$–$C_6$ alkyl)C(O)O ($C_1$–$C_6$ alkyl), —($C_1$–$C_6$ alkoxy)C(O)($C_1$–$C_6$ alkyl), —C(O)($C_1$–$C_6$ alkyl), —N($C_1$–$C_6$ alkyl)($C_1$–$C_6$ alkyl), —C(O)NH($C_1$–$C_6$ alkyl), —NHC(O)H, and —NHC (O)($C_1$–$C_6$ alkyl);

$R^{13}$ is hydrogen, phenyl or $C_1$–$C_6$ alkyl;

$R^{14}$ and $R^{15}$ are each independently selected from hydrogen, hydroxy, halo, amino, carboxy, cyano, hydroxy-substituted $C_1$–$C_6$ alkyl, $C_1$–$C_6$ alkoxy, —($C_1$–$C_6$ alkyl)-($C_1$–$C_6$ alkoxy), —NH($C_{1-C6}$ alkyl), —C(O)O($C_1$–$C_6$ alkyl), —OC(O)($C_1$–$C_6$ alkyl), —($C_1$–$C_6$ alkyl)C(O)($C_1$–$C_6$ alkyl), —($C_1$–$C_6$ alkyl)C (O)O($C_1$–$C_6$ alkyl), —($C_1$–$C_6$ alkoxy)C(O)($C_1$–$C_6$ alkyl), —C(O)($C_1$–$C_6$ alkyl), —N($C_1$–$C_6$ alkyl)($C_1$–$C_6$ alkyl), —C(O)NH($C_1$–$C_6$ alkyl), —NHC(O)H, —NHC (O)($C_1$–$C_6$ alkyl), and the radicals set forth in the definition of $R^{12}$;

$R^{16}$ is —NHC(O)$R^{18}$, —NHCH$_2R^{18}$, —$SO_2R^{18}$, —$CO_2$H or one of the radicals set forth in any of the definitions of $R^{12}$, $R^{14}$, and $R^{15}$;

$R^{17}$ is oximino (=NOH) and $R^{16}$ is absent, or $R^{17}$ is one of the radicals set forth in any of the definitions of $R^{12}$, $R^{14}$, and $R^{15}$; and, $R^{18}$ is $C_1$–$C_6$ alkyl, hydrogen, phenyl or —($C_1$–$C_6$ alkyl) (phenyl);

with the proviso that (a) when m is 0, then one of $R^{16}$ and $R^{17}$ is absent and the other is hydrogen; and (b) when $R^{14}$ and $R^{15}$ are attached to the same carbon atom, then $R^{14}$ and $R^{15}$ are each independently selected from hydrogen, fluoro, $C_1$–$C_6$ alkyl, hydroxy-substituted $C_1$–$C_6$ alkyl and —($C_1$–$C_6$ alkyl)-($C_1$–$C_6$ alkoxy).

2. A compound according to claim 1 wherein W is $C_1$–$C_3$ alkoxy optionally substituted with 1 to 3 fluoro substituents, Q is —N($C_1$–$C_6$ alkyl)-, and $R^1$ is thiazol-5-yl.

3. A compound according to claim 1 wherein $R^{12}$ is phenyl, each of $R^{13}$, $R^{14}$, $R^{15}$ and $R^{16}$ is hydrogen, m is zero, and X is —$(CH_2)_3$—.

4. A compound according to claim 3 wherein $R^1$ is 2,4-dimethyl-thiazol-5-yl, W is isopropoxy or methoxy optionally substituted with 1 to 3 fluoro substituents, and Q is —$SO_2$N($CH_3$)— or —$SO_2$N(CH($CH_3$)$_2$)—.

5. A compound according to claim 1 that is selected from:

2,4-dimethylthiazole-5-sulfonic acid [4-methoxy-3-((2S, 3S)-2-phenylpiperidin-3-ylaminomethyl)phenyl]-methylamide;

N-(4,5-dimethylthiazol-2-yl)-N-[4-methoxy-3-((2S,3S)-2-phenylpiperidin-3-yl-aminomethyl)phenyl]-methanesulfonamide;

{5-[(4,5-dimethylthiazol-2-yl)methylamino]-2-methoxybenzyl}-((2S,3S)-2-phenylpiperidin-3-yl)amine;

{5-(4,5-dimethylthiazol-2-ylamino)-2-methoxybenzyl}-((2S,3S)-2-phenylpiperidin-3-yl)amine;

4,5-dimethylthiazole-2-sulfonic acid methyl-[3-((2S,3S)-2-phenylpiperidin-3-ylaminomethyl)-4-trifluoromethoxyphenyl]-amide;

2,4-dimethylthiazole-5-sulfonic acid [4-isopropoxy-3-((2S, 3S)-2-phenylpiperidin-3-ylaminomethyl)phenyl]-methylamide;

2,4-dimethylthiazole-5-sulfonic acid [4-isopropoxy-3-((2S, 3S)-2-phenylpiperidin-3-ylaminomethyl)phenyl]-isopropylamide;

2,4-dimethylthiazole-5-sulfonic acid [4-methoxy-3-((2S, 3S)-2-phenylpiperidin-3-ylaminomethyl)phenyl]-isopropylamide;

2,4-dimethylthiazole-5-sulfonic acid [4-methoxy-3-((2S, 3S)-2-phenylpiperidin-3-ylaminomethyl)phenyl]-isobutylamide; and 2,4-dimethylthiazole-5-sulfonic acid [4-isopropoxy-3-((2S, 3S)-2-phenylpiperidin-3-ylaminomethyl)phenyl]-isobutylamide.

6. A pharmaceutical composition for treating or preventing a condition selected from the group consisting of inflammatory diseases, anxiety, colitis, depression or dysthymic disorders, urinary incontinence, gastrointestinal disorders, psychosis, pain, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising an amount of a compound according to claim 1 effective in preventing or treating such condition and a pharmaceutically acceptable carrier.

7. A method of treating or preventing a condition selected from the group consisting of inflammatory diseases anxiety, colitis, depression or dysthymic disorders, urinary incontinence, gastrointestinal disorders, psychosis, pain, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising administering to a mammal in need of such treatment or prevention an amount of a compound according to claim 1 effective in preventing or treating such condition.

8. A pharmaceutical composition for antagonizing the effects of substance P in a mammal, comprising a substance P antagonizing effective amount of a compound according to claim 1 and a pharmaceutically acceptable carrier.

9. A method of antagonizing the effects of substance P in a mammal, comprising administering to said mammal a substance P antagonizing effective amount of a compound according to claim 1.

10. A pharmaceutical composition for treating or preventing a condition in a mammal, the treatment or prevention of which is effected or facilitated by a decrease in substance P mediated neurotransmission, comprising an amount of a compound according to claim 1 effective in antagonizing the effect of substance P at its receptor site and a. pharmaceutically acceptable carrier.

11. A method of treating or preventing a condition in a mammal, the treatment or prevention of which is effected or facilitated by a decrease in substance P mediated neurotransmission, comprising administering to a mammal in need of such treatment or prevention an amount of a compound according to claim 1, or a pharmaceutically acceptable salt thereof, effective in antagonizing the effect of substance P at its receptor site.

12. A pharmaceutical composition for treating or preventing a condition in a mammal, the treatment or prevention of which is effected or facilitated by a decrease in substance P mediated neurotransmission, comprising an amount of a compound according to claim 1, or a pharmaceutically acceptable salt thereof, effective in treating or preventing such condition and a pharmaceutically acceptable carrier.

13. A method of treating or preventing a condition in mammal, the treatment or prevention of which is effected or facilitated by a decrease in substance P mediated neurotransmission, comprising administering to a mammal in need of such treatment or prevention an amount of a compound according to claim 1 effective in treating or preventing such condition.

* * * * *